United States Patent
Garel et al.

(10) Patent No.: US 8,933,274 B2
(45) Date of Patent: Jan. 13, 2015

(54) METHOD FOR PREPARING A VANILLIN DERIVATIVE

(71) Applicant: Rhodia Operations, Aubervilliers (FR)

(72) Inventors: Laurent Garel, Lyons (FR); Martine Vibert, Lyons (FR); Corine Cochennec, Voiron (FR); François Metz, Irigny (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 14/349,842

(22) PCT Filed: Oct. 5, 2012

(86) PCT No.: PCT/EP2012/069732
§ 371 (c)(1),
(2) Date: Apr. 4, 2014

(87) PCT Pub. No.: WO2013/050537
PCT Pub. Date: Apr. 11, 2013

(65) Prior Publication Data
US 2014/0323769 A1   Oct. 30, 2014

(30) Foreign Application Priority Data

Oct. 6, 2011   (FR) ..................................... 11 59007

(51) Int. Cl.
C07C 45/71   (2006.01)
C07C 45/64   (2006.01)

(52) U.S. Cl.
CPC ..................... *C07C 45/64* (2013.01)
USPC ....................................................... 568/433

(58) Field of Classification Search
USPC ....................................................... 568/433
See application file for complete search history.

(56) References Cited

U.S. PATENT DOCUMENTS 5,811,587 A   9/1998   Moreau et al.

FOREIGN PATENT DOCUMENTS

WO   WO 96/37452 A1   11/1996

OTHER PUBLICATIONS

Xu, H., et al—"Reactivity of Lignin Diphenylmethane Model Dimers 1. Nitrobenzene Oxidation", 1998, Holzforschung, vol. 52, Issue No. 1, pp. 51-56, XP 055026616; 6 pgs.
Schwarz, Bernd, et al—"Identification of Novel Orosensory Active Molecules in Cured Vanilla Beans", 2009, Journal of Agricultural and Food Chemistry, vol. 57, pp. 3729-3737, XP 055026540; 9 pgs.

*Primary Examiner* — Sikarl Witherspoon
(74) *Attorney, Agent, or Firm* — Beatrice C. Ortego

(57) ABSTRACT

A method for preparing a compound of formula (I) which is a vanillin derivative, of dimer type, called 3-(4-hydroxy-3-methoxybenzyl)-4-hydroxy-5-methoxybenzaldehyde, such method comprising a reaction of vanillin and vanillyl alcohol in the presence of a base.

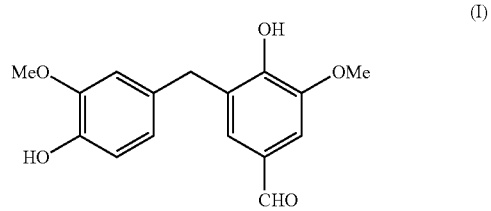

(I)

13 Claims, No Drawings

METHOD FOR PREPARING A VANILLIN DERIVATIVE

METHOD FOR PREPARING A VANILLIN DERIVATIVE

The present application is a U.S. national stage entry under 35 U.S.C. §371 of International Application No. PCT/EP2012/069732 filed Oct. 5, 2012, which claims priority to French Application No. 11.59007 filed on Oct. 6, 2011, the whole content of this application being herein incorporated by reference for all purposes.

The subject of the present invention is a process for preparing a vanillin derivative, of dimer type, called 3-(4-hydroxy-3-methoxybenzyl)-4-hydroxy-5-methoxybenzaldehyde.

Vanillin is a product widely used in many fields of application as a flavoring and/or fragrance.

Thus, vanillin is abundantly consumed in the food and animal industry, but it also has applications in other fields, for instance pharmacy or perfumery.

The processes currently used to prepare vanillin can produce by-products in trace amounts, among which is in particular 3-(4-hydroxy-3-methoxybenzyl)-4-hydroxy-5-methoxybenzaldehyde.

As it happens, this by-product of formula 3-(4-hydroxy-3-methoxybenzyl)-4-hydroxy-5-methoxybenzaldehyde has advantageous sensory properties.

However, there is at the current time no process for preparing 3-(4-hydroxy-3-methoxybenzyl)-4-hydroxy-5-methoxybenzaldehyde as such with a satisfactory yield.

The objective of the present invention is to provide a novel process for preparing 3-(4-hydroxy-3-methoxybenzyl)-4-hydroxy-5-methoxybenzaldehyde.

The objective of the present invention is to provide a process which makes it possible to obtain 3-(4-hydroxy-3-methoxybenzyl)-4-hydroxy-5-methoxybenzaldehyde with a satisfactory yield.

Thus, the present invention relates to a process for preparing a compound of formula (I) below:

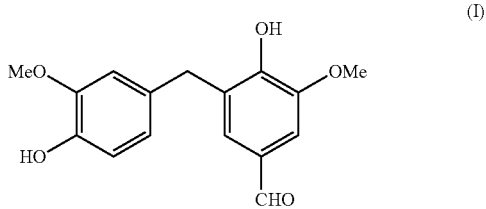 [SMILES: COc1cc(Cc2cc(C=O)cc(OC)c2O)ccc1O]

comprising the reaction of vanillin and vanillyl alcohol in the presence of a base.

Vanillin or 4-hydroxy-3-methoxybenzaldehyde is a molecule which is well known in the prior art, corresponding to the formula below:

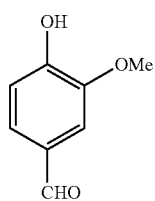 [SMILES: COc1cc(C=O)ccc1O]

Vanillyl alcohol or 4-hydroxy-3-methoxybenzyl alcohol is a molecule which is well known in the prior art, corresponding to the formula below:

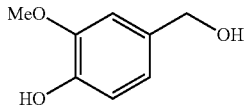

The present invention is based on an addition reaction of vanillyl alcohol (VOH) with vanillin (VA) in the presence of a base.

It has been observed, surprisingly, that the aldehyde function of vanillin remains unchanged. In the context of the process of the invention, this function does not react with the alcohol function of vanillyl alcohol.

According to one embodiment, the base is selected from the group consisting of inorganic bases, organic bases, inorganic heterogeneous bases, and mixtures thereof.

By way of organic bases, mention may in particular be made of tertiary amines, for example trimethylamine, triethylamine, tripropylamine, tributylamine, N,N-diisopropylethylamine, N-methylmorpholine, N-ethylmorpholine, N-propylmorpholine and 1-methylpyrrolidone. Use may also be made of nitrogenous anionic bases, for example salts, in particular alkali or alkaline-earth metal salts, of amines, which may or may not be silylated, and also silylamines. Salified disilylamines, and especially the salts, in particular alkali or alkaline-earth metal salts, of hexamethyldisilazane (HMDZ), are also appropriate.

By way of inorganic heterogeneous bases, mention may in particular be made of magnesium dioxide $MgO_2$.

Preferably, the reaction step of the process is carried out in the presence of an inorganic base.

According to one embodiment, the base is selected from the group consisting of alkali metal hydroxides, alkaline-earth metal hydroxides, alkali metal bicarbonates, alkaline-earth metal bicarbonates, alkali metal hydrogen carbonates, alkaline-earth metal hydrogen carbonates, alkali metal phosphates, alkaline-earth metal phosphates, alkali metal hydrogen phosphates and alkaline-earth metal hydrogen phosphates, and mixtures thereof.

By way of preferred inorganic bases, mention may be made of LiOH, CsOH, NaOH, KOH, $Na_2CO_3$ or $NaHCO_3$. Preferentially, $Na_2CO_3$ is used as base.

According to the process of the invention, the abovementioned reaction step can be carried out in the presence of a solvent.

By way of solvent, mention may be made of aqueous and organic solvents, and mixtures thereof.

Preferably, the process of the invention is carried out in an aqueous medium: the process according to the present invention is preferably carried out in the presence of water as solvent.

In the context of the process of the invention, when the base used is an organic base, the reaction is carried out in the presence of an organic solvent. A solvent which is inert under the reaction conditions is selected. Said solvent is, for is example, selected from nonpolar organic solvents such as aliphatic hydrocarbons (preferentially alkanes of formula $C_nH_{2n+2}$ with n=6 to 14), cycloaliphatic hydrocarbons such as cyclohexane, aromatic hydrocarbons (preferentially benzene, toluene, xylenes, ethylbenzene, diethylbenzenes, trimethylbenzenes or cumene), aliphatic or aromatic halogenated hydrocarbons, in particular perchlorinated hydrocarbons (preferentially trichloromethane or tetrachloromethane) and partially chlorinated hydrocarbons (such as dichloromethane, tetrachloroethane, monochlorobenzene or dichlorobenzenes). Said organic solvent is also advantageously selected from polar aprotic organic solvents, for example dimethylformamide or dimetylacetamide. It may also be very preferentially selected from polar protic solvents such as alcohols, in particular ethanol.

According to one embodiment, the process of the invention is carried out in any two-phase medium, i.e. in the presence of water and of an organic solvent, preferentially an insoluble organic solvent. According to this embodiment, the ratio between the volume of organic solvent and the volume of water is included from 0.1 to 10 and preferably from 0.5 to 1.5.

The reaction of the process of the invention is carried out at a temperature included from 0° C. to 100° C. and preferably from 30° C. to 80° C.

Preferably, in the context of the present invention, the reaction is carried out at a pH included from 7 to 14 and preferably from 8 to 10.

The present invention also relates to a preparation process as defined above, in which the ratio between the number of moles of vanillin and the number of moles of vanillyl alcohol ([VA/VOH]$_{mol}$) is included from 0.5 to 20, preferably from 1 to 15, preferentially from 2 to 5 and in particular from 3 to 5.

According to one advantageous embodiment of the process of the invention, the ratio between the number of moles of base and the sum of the number of moles of vanillin and of the number of moles of vanillyl alcohol is included from 0.1 to 10, preferably from 0.5 to 6 and preferentially from 0.7 to 2. Preferentially, this ratio is in the region of 1 and very preferentially equal to 1.

According to one embodiment, in the context of the process of the invention, when the reaction is carried out in the presence of water, the ratio between the weight of vanillin and of vanillyl alcohol and the weight of water is included from 0.05 to 0.5 and preferably from 0.1 to 0.3.

The process of the invention consists of a reaction between vanillin and vanillyl alcohol in the presence of a base. These various reagents, namely the vanillin, the vanillyl alcohol and the base, can be brought together by any means is known to those skilled in the art.

Likewise, these reagents can be introduced in any order.

The solvent may also be introduced in any order with respect to the reagents.

The reagents and also the solvent may also be introduced once or several times, i.e. in fractions.

According to one embodiment, the solvent, in particular water, can be added to a mixture comprising the base and the vanillin and then the alcohol can subsequently be added.

According to another embodiment, the base can be added several times. For example, the solvent, in particular water, can be added to a mixture comprising the base and the vanillin and then the alcohol and the base can subsequently be added simultaneously.

After the process of the invention, a liquid solution comprising 3-(4-hydroxy-3-methoxybenzyl)-4-hydroxy-5-methoxybenzaldehyde is obtained.

This compound can then be subjected to subsequent conventional separation steps, in particular separation by distillation.

The compound obtained by means of the process of the invention is advantageously used in food compositions, i.e. compositions intended to be consumed by human beings.

It has an effect of fullness in the mouth, and such an effect is sought in order to compensate for the insipid nature of many food products which have low fat and sugar contents. This effect of fullness in the mouth gives the consumer a pleasant sensation in the mouth, in particular through a creamy nature, a milk fat nature and/or a sweet nature.

It can, for example, be used in a combination of flavorings, in particular food flavorings, comprising compounds such as vanillin or ethyl vanillin. The compound obtained according to the process of the invention is advantageously incorporated into food compositions which are in liquid form, in particular beverages, milk and soups, or in semi-solid or solid form, in particular yoghurts, margarines, instant desserts and ice creams, cookies and cakes, confectionery products and chocolate products.

Thus, the 3-(4-hydroxy-3-methoxybenzyl)-4-hydroxy-5-methoxybenzaldehyde is advantageously used to confer or reinforce certain taste sensations.

Examples illustrating the present invention are given below, with no limiting nature.

EXAMPLES

In the examples, the percentages mentioned are expressed by weight.

The reagents used, namely vanillin, vanillyl alcohol and sodium carbonate $Na_2CO_3$, are introduced simultaneously.

The reactions are carried out in the presence of water.

The tables below indicate the operating conditions implemented and also the amounts of the various reagents used.

| | VA (mmol) | VOH (mmol) | VA/ VOH molar ratio | $Na_2CO_3$ base (mmol) | T (° C.) | base (mmol)/ VA + VOH (mmol) | 1 (mmol) |
|---|---|---|---|---|---|---|---|
| Ex. 1 | 6.71 | 5.19 | 1.29 | 12.29 | 35 | 1.03 | 0.89 |
| Ex. 2 | 12.10 | 5.10 | 2.37 | 17.08 | 40 | 0.99 | 1.19 |

| | VA (g) | VOH (g) | water (g) | VA (g) + VOH (g)/water (g) | CR VA (%) | CR VOH (%) | YLD 1 (%) |
|---|---|---|---|---|---|---|---|
| Ex. 1 | 1.02 | 0.8 | 20.39 | 0.09 | 20 | 89 | 66 |
| Ex. 2 | 1.84 | 0.78 | 21.00 | 0.12 | 13 | 62 | 76 |

VA: vanillin
VOH: vanillyl alcohol
1: 3-(4-hydroxy-3-methoxybenzyl)-4-hydroxy-5-methoxybenzaldehyde
CR: conversion rate (represents the amount of reagent converted relative to the amount of reagent introduced)
YLD: yield (ratio between the number of moles of compound 1 obtained and the number of moles of vanillin converted)

Thus, the process of the invention makes it possible to obtain the compound 3-(4-hydroxy-3-methoxybenzyl)-4-hydroxy-5-methoxybenzaldehyde with a very satisfactory yield.

The invention claimed is:
1. A process for preparing a compound of formula (I) below:

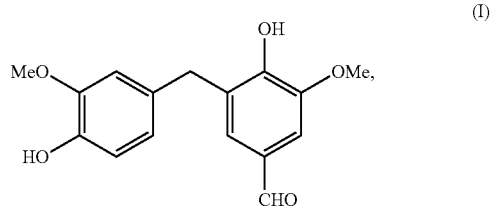 [SMILES: COc1cc(Cc2cc(C=O)cc(OC)c2O)ccc1O]

comprising a reaction of vanillin and vanillyl alcohol in the presence of a base.

2. The process as claimed in claim 1, wherein said base is selected from the group consisting of inorganic bases, organic bases, inorganic heterogeneous bases, and mixtures thereof.

3. The process as claimed in claim 2, wherein said base is selected from the group consisting of alkali metal hydroxides, alkaline-earth metal hydroxides, alkali metal bicarbonates, alkaline-earth metal bicarbonates, alkali metal hydrogen carbonates, alkaline-earth metal hydrogen carbonates, alkali metal phosphates, alkaline-earth metal phosphates, alkali metal hydrogen phosphates, alkaline-earth metal hydrogen phosphates, and mixtures thereof.

4. The process as claimed in claim 1, wherein said reaction is carried out in the presence of a solvent.

5. The process as claimed in claim 4, wherein said solvent is selected from the group consisting of aqueous solvents, organic solvents, and mixtures thereof.

6. The process as claimed in claim 4, wherein said solvent is water.

7. The process as claimed in claim 1, wherein said reaction is carried out at a temperature included from 0° C. to 100° C.

8. The process as claimed in claim 1, wherein said reaction is carried out at a pH included from 7 to 14.

9. The process as claimed in claim 1, wherein a molar ratio between the number of moles of said vanillin and the number of moles of said vanillyl alcohol of from 0.5 to 20 is used in said reaction.

10. The process as claimed in claim 1, wherein a molar ratio between the number of moles of said base and the sum of the number of moles of said vanillin and of the number of moles of said vanillyl alcohol of from 0.1 to 10 is used in said reaction.

11. The process as claimed in claim 6, wherein a weight ratio between the weight of said vanillin and of said vanillyl alcohol and the weight of said water of from 0.05 to 0.5 is used in said reaction.

12. The process as claimed in claim 1, wherein said base is selected from the group consisting of LiOH, CsOH, NaOH, KOH, $Na_2CO_3$, and $NaHCO_3$.

13. The process as claimed in claim 1, wherein a liquid solution comprising said compound of Formula (I) is obtained.

* * * * *